United States Patent [19]

Baker et al.

[11] Patent Number: 4,906,581
[45] Date of Patent: Mar. 6, 1990

[54] METHOD OF QUALITY CONTROL FOR HOLLOW FIBER GAS TRANSFER CELLS

[75] Inventors: Daniel A. Baker, Minnetonka; Louis C. Cosentino; LeRoy J. Fischbach, both of Plymouth; Robert T. Hall, II, Welch; Anatol M. Hnojewyj, Minneapolis; Scott R. Vagle, Blaine; Perry L. Blackshear, Jr., Mahtomedi, all of Minn.

[73] Assignee: Minntech Corporation, Minneapolis, Minn.

[21] Appl. No.: 260,448

[22] Filed: Oct. 20, 1988

[51] Int. Cl.⁴ .......................................... G01N 25/20
[52] U.S. Cl. ................................... 436/147; 422/108; 436/2; 436/8; 436/55; 436/183
[58] Field of Search ..................... 436/2, 8, 147, 183, 436/55; 422/108

[56] References Cited

U.S. PATENT DOCUMENTS 4,791,054 12/1988 Hamada et al. ................ 422/46 X

Primary Examiner—Robert J. Hill, Jr.
Assistant Examiner—Marcella I. Fruchter
Attorney, Agent, or Firm—Vidas & Arrett

[57] ABSTRACT

A method for non-destructive testing for approximation of oxygen transmission in hollow fiber blood oxygenators or the like is provided which method includes passing a first fluid at a predetermined temperature and volume flow rate through the hollows of the fibers and a second fluid at a second predetermined input temperature and volume flow rate across the outside of the fibers and measuring the heat rise or fall of the fluids and comparing the results with standards for a given blood oxygenator device.

8 Claims, 1 Drawing Sheet

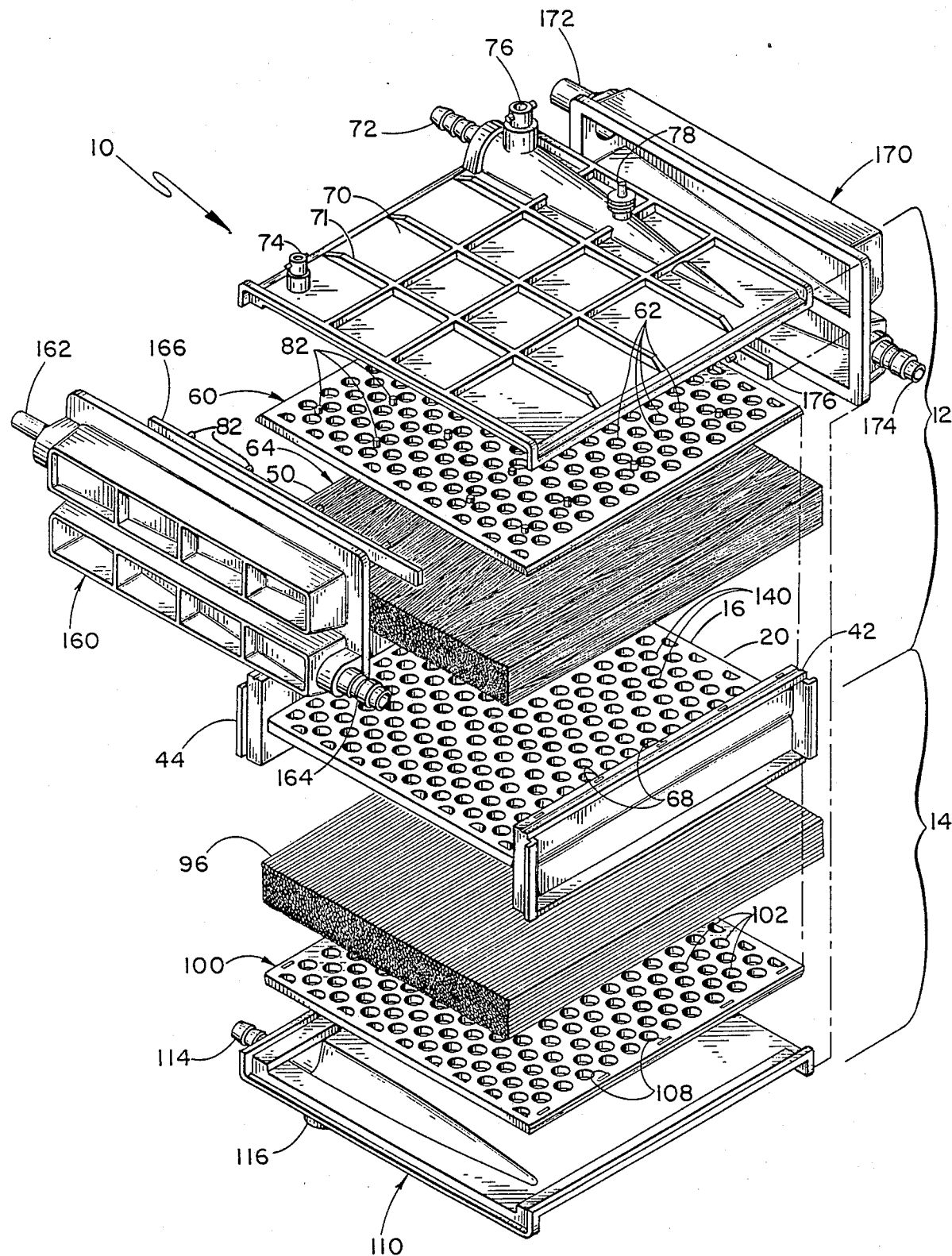

METHOD OF QUALITY CONTROL FOR HOLLOW FIBER GAS TRANSFER CELLS

BACKGROUND OF THE INVENTION

1. Field of the Invention

This invention relates to gas transfer systems and more particularly to the measuring of the gas transfer capabilities of such systems from one device to an other without having the test itself destructive of the systems. More particularly, it relates to blood oxygenators where the non-destructive testing permits a quality control of manufactured devices not heretofore available.

2. Description of the related art

The prior art known to the inventors consist of destructive testing of blood oxygenators and the extrapolation of the data to comparable units that have not been tested. No search has been made in accordance with 35 CFR (1.56(a).

SUMMARY OF THE INVENTION

It will be understood that the invention will be described with respect to a blood oxygenator system although it is contemplated that the principles of the method of the invention can be extended to other gas transfer devices.

Blood oxygenators have found extensive usage in the treatment of patients during surgery. One type of oxygenator utilizes a plurality of hollow fibers of a material such as polyethylene through which oxygen is passed, while at the same time, blood is flowed transversely to the length of the fibers over the fibers and is oxygenated during the course of such passage. Such oxygenators can be destructively tested by actually running them with blood and measuring the effective oxygenation of the blood during a simulated oxygenation step such as one would use with the actual patient. However, such tests are destructive as the oxygenator cannot be cleaned and reused with human patients after such testing Therefore, the data obtained from destructive testing can only be extrapolated to approximate its effectiveness with identical geometrical constructions of oxygenators.

In accordance with the present invention a method is provided wherein the hollow fibers are used to carry a first fluid at a first temperature and flow volume through the interiors thereof while simultaneously a second fluid at a second different temperature and second flow volume is passed over and transverse to length the outside of the fibers. A measure is made of the steady state condition of the fluids passing through the system to measure the gain or loss in temperature in at least one of the fluid due to heat transfer across the walls of the fiber. This change in temperature is compared to known oxygenator device's heat transfer under the the same test conditions where actual oxygenation deficiency is known. A highly useful approximation can be made that is sufficiently accurate for purposes of quality control to eliminate those devices whose apparent efficiency of oxygenation is below or likely to be below that of acceptable devices. Typically, highly pure water is utilized as the heat carrying fluids in both the interior and exterior portions of the oxygenator during testing. Temperature differentials at the start between the two fluids will typically be about 15 degrees C.

BRIEF DESCRIPTION OF THE DRAWINGS

FIG. 1 is an exploded view of a blood oxygenator presently marketed showing the major elements of the construction.

DESCRIPTION OF THE PREFERRED EMBODIMENTS

Turning to the FIGURE, FIG. 1 is an exploded view of an oxygenator from the copending patent application of the same assignee as the present invention. [PCT Ser. No. 87/01850 filed July 28, 1987] This oxygenator will be described in its testing in accordance with the present invention.

It should be understood that while the invention will be described with particularity with respect to that configuration, other oxygenators will also find the invention usable as a quality control. It is anticipated that the principal advantages of the invention will be found with hollow core fiber oxygenators, rather than the flat membrane type oxygenators.

The device of FIG. 1 comprises basic elements of a pack of hollow core fibers 64 that in use as an oxygenator are used for passage of oxygen therethrough and which have passage of blood to be oxygenated moving transversely across the fibers. Oxygen enters at port 162 and exists at port 172. A pack of hollow core fibers of a predetermined packing density (typically 50 -55% of the available cross-sectional area) is used for such purpose.

A second pack of hollow core fibers 96 is used as heat exchange fibers to adjust the temperature of the blood to the desired level. No oxygenation is provided by this second set of fibers.

Blood flow is accomplished by entry at port 72 and passage of blood through the unit transversely to the lengths of the fiber and exiting at port 114.

In the methodology in the invention, rather than passage of oxygen and blood, water at a first predetermined temperature will pass through the hollows of the fibers at a first volume flow rate. A second source of water at a different predetermined temperature will pass transversely in the same pattern as the blood is intended to do across the hollow core fibers. Suitable temperature measuring means (not shown) are provided for measuring the temperature differential of the exiting waters after a steady state condition is reached. A measure of the amount of heat transfer measured by temperature change has been found to be a reliable reasonable predictor of the effectiveness of an individual oxygenator device for its intended purpose of oxygenating blood. A minimum performance guide is used to reject devices that are low in heat transfer and anticipated to be below desired oxygenation efficiency.

PREFERRED DESCRIPTION

In the application of the method to a device as illustrated in FIG. 1, it must be understood that the bundle of fibers 64 and bundle 96 have the ends encapsulated in a manner known in the art to leave the cores open. The entire exploded assembly is, of course, joined to provide a series of separate, sealed from one another, chambers. In the actual testing procedure, highly pure water is preheated to a temperature which may conveniently be 29 degrees C. A pressure is maintained on this heated water to insure a flow rate of approximately 0.5 gallons per minute through port 162 and then through the hollow portion of fibers 64 until it exists at port 172. The water that is passed through the hollow fibers 64 and has had heat either given up or absorbed, as will be described, is measured at the point of exit to determine the change in temperature that has resulted in passage through the fibers. This path of flow, as noted previously corresponds to the typical usage of the oxygenator with the blood flowing on the outside of the fibers and oxygen flowing through the center.

Simultaneous with the passage of the heated water through port 162 and through the fibers, a separate source of water at approximately 12 degrees C. is passed through port 72 and is then spread out across the surface of plate 60 and thence passes transversely down through fibers 64 until it reaches a lower plate 110 and exits through port 114. As the heat exchange fibers 96 do not have any fluid passing therethrough, they have no function in the test procedure as described once an equilibrium condition is reached. Measuring means, (not shown) are provided at exit port 114 to measure the change in the temperature of the water passing transversely across the fibers. As illustrations of the exit temperatures for the oxygen path and for the blood path, typically the exit temperature for the oxygen path will be about 18 degrees C. while that for the blood path will be about 26 degrees. These numbers will vary dependent upon a number of factors, including the effectiveness of heat transfer from the hotter to the cooler fluid through the collective walls of the individual hollow core fibers.

It should be understood that the temperature of the fluids as being warmer for that following the oxygen path and cooler to start for the that of the blood flow path can be reversed so that the cooler water flows through the hollow fibers and the warmer water flows around the hollow fibers. The important consideration is that there be a temperature differential at the start so that measurement can be made of the Nusselt effectiveness of the heat transfer during the test conditions. Similarly, the flow rates can be changed from the specific example given above to be either higher or lower. For economy, it is desirable to keep the flow rates at the approximate figures given above and under conditions which will give the larger flow rate to the warmer water.

A number of tests were run following the principles described above on a group of oxygenator devices as illustrated in FIG. 1. The heat transfer characteristics under the conditions illustrated were compared between the individual cells. The individual cells after a testing for the heat transfer characteristics were run under the close simulation of actual use in oxygenation of human blood using oxygen through the fibers and animal blood passing across the fibers in its normal manner of usage. The oxygen transfer characteristics and actual blood testing (PO2) were compared with the heat exchanger Nusselt effectiveness for a number of cells as indicated below. It was found that for those cells that are considered to be marginal in their oxygen efficiency (i.e., with a value below 150) that the heat transfer effectiveness was below about 70%. For those oxygenator devices which showed PO2 values in excess of 150, there was a strong correlation between the heat transfer effectiveness and the oxygenation effectiveness of the device.

| HEAT EXCHANGE NUSSELT EFFECTIVENESS VS PO2 | | | |
|---|---|---|---|
| Oxygenator | PO2 | Run 1 | Run 2 |
| #1 | 68.4 | 66.4 | 62.9 |
| #2 | 141 | 71 | 72 |
| #3 | 167 | 80.6 | 87.5 |
| #4 | 168 | 84.7 | 81.1 |
| #5 | 176 | 88.2 | 88.7 |
| #6 | 180 | 81 | 82.2 |
| #7 | 194 | 81.8 | 76.8 |
| #8 | 220 | 81.3 | 83 |
| #9 | 250 | 88.2 | 91 |
| #10 | 264 | 86.1 | 86.4 |
| #11 | 284 | 86.5 | 84 |
| #12 | 286 | 87 | 87 |
| #13 | 316 | 92.2 | 90 |
| #14 | 324 | 90 | 92.4 |

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of quality control of the efficacy of a hollow fiber gas transfer cell comprising:
   (a) passing a first stream of fluid at a first inlet predetermined temperature, $T_2$ through the interiors of individual hollow core fibers of a bundle of hollow core fibers in said cell at a first volume flow rate;
   (b) passing a second stream of fluid at an inlet temperature $T_3$ that is different than $T_1$ transversely and outside of the individual fibers of said bundle of hollow core fibers;
   (c) measuring the exit temperature $T_2$ of one of said streams of fluid; and
   (d) comparing the temperature change of at least one of said streams of fluid and rejecting the cell if it has a heat transfer Nusselt effectiveness below a predetermined level.

2. The method in accordance with claim 1 wherein $T_1$ is about 15 degrees C. different than $T_3$.

3. The method in accordance with claim 1 wherein $T_1$ is at a higher temperature than $T_3$.

4. The method in accordance with claim 1 wherein the fluids are water.

5. The method in accordance with claim 1 wherein $T_1$ is about 29 degrees C. and $T_3$ is about 12 degrees C.

6. The method in accordance with claim 1 wherein the cell is rejected if it has a Nusselt effectiveness below about 70.

7. The method in accordance with claim 5 wherein the flow rate of said first stream is about 0.5 gallon per minute and the flow rate of said second stream is about 0.25 gallons per minute.

8. The method in accordance with claim 7 wherein $T_1$ is about 29 degrees C. and $T_3$ is about 12 degrees C.

* * * * *